United States Patent
Saito et al.

(10) Patent No.: US 7,294,609 B2
(45) Date of Patent: Nov. 13, 2007

(54) CLEANSING FOAM AGENT COMPRISING A POLYGLYCERIN MONOCARBOXYLATE AND HINOKITIOL BACTERICIDE

(75) Inventors: Yoshinobu Saito, Osaka (JP); Masahito Tanaka, Osaka (JP); Takahiro Okuda, Osaka (JP); Tetsuo Nishina, Osaka (JP); Kazuo Iwai, Shiga (JP)

(73) Assignees: P& PF Co., Ltd., Ibaraki-shi (JP); JCS Inc., Osaka-shi (JP)

( * ) Notice: Subject to any disclaimer, the term of this patent is extended or adjusted under 35 U.S.C. 154(b) by 67 days.

(21) Appl. No.: 11/155,573

(22) Filed: Jun. 20, 2005

(65) Prior Publication Data

US 2006/0019855 A1    Jan. 26, 2006

(30) Foreign Application Priority Data

Jun. 21, 2001   (JP)   ............................ 2004-182690

(51) Int. Cl.
 *C11D 3/48*   (2006.01)
 *C11D 1/66*   (2006.01)

(52) U.S. Cl. .................. 510/138; 510/130; 510/131; 510/135; 510/149; 510/382; 510/437

(58) Field of Classification Search ................ 510/130, 510/138, 131, 135, 149, 382, 437
See application file for complete search history.

(56) References Cited

U.S. PATENT DOCUMENTS

| | | | | |
|---|---|---|---|---|
| 4,547,365 A | * | 10/1985 | Kubo et al. | 424/70.5 |
| 4,745,103 A | * | 5/1988 | Oono et al. | 514/23 |
| 4,985,425 A | * | 1/1991 | Chiba et al. | 514/222.2 |
| 5,676,957 A | * | 10/1997 | Nakamura et al. | 424/401 |
| 6,025,312 A | * | 2/2000 | Saito et al. | 510/130 |
| 6,190,679 B1 | * | 2/2001 | Takekoshi et al. | 424/401 |
| 2003/0068968 A1 | | 4/2003 | Iwai | |
| 2004/0247551 A1 | * | 12/2004 | Yokomaku et al. | 424/70.13 |

FOREIGN PATENT DOCUMENTS

| | | |
|---|---|---|
| JP | 8183997 | 7/1996 |
| JP | 200002901129 | 10/2000 |
| JP | 2000342236 | 12/2000 |
| JP | 2001131061 | 5/2001 |
| JP | 2002238524 | 8/2002 |
| JP | 3391403 | 1/2003 |
| JP | 2003-102373 | 4/2003 |
| JP | 2004016196 | 1/2004 |

* cited by examiner

*Primary Examiner*—Charles Boyer
(74) *Attorney, Agent, or Firm*—Mots Law, PLLC; Marvin A. Motsenbocker

(57) ABSTRACT

A composition for a bactericidal, disinfecting, and cleansing foam agent contains, as essential components, (a) at least one nonionic surfactant selected from polyalkylene glycol ethers and fatty acid esters of polyglycerin, (b) a bactericidal component, and (c) water.

In a preferable embodiment, the nonionic surfactant has a HLB of 10 or greater and is selected from fatty acid esters of polyglycerin. The bactericidal component is selected from hinokitiol, hinokitiol salts, and hinokitiol complexes. This composition is free from a lower alcohol, and further free from an anionic surfactant, an amphoteric surfactant and a cationic surfactant. This composition is particularly suitable for a pump foam-type product.

This invention can provide a composition suitable for a bactericidal, disinfecting, and cleansing agent wherein the composition turns into foam sufficiently to give an easy-to-use foam agent.

6 Claims, No Drawings

CLEANSING FOAM AGENT COMPRISING A POLYGLYCERIN MONOCARBOXYLATE AND HINOKITIOL BACTERICIDE

CROSS-REFERENCE TO RELATED APPLICATION/PRIORITY

This nonprovisional application claims priority under 35 U.S.C. §119(a) on patent application Ser. No. 2004-182690 filed in Japan on Jun. 21, 2004, the entire contents of which are hereby incorporated by reference.

FIELD OF THE INVENTION

The present invention relates to a composition for a bactericidal, disinfecting, and cleansing foam agent which requires no wash-off and wipe-off operation.

BACKGROUND ART

Hinokitiol (chemical name: 4-isopropyl-2-hydroxy-cyclohepta-2,4,6-triene-1-on) is extracted from natural products such as hinoki oil and hiba oil, or is chemically synthesized. Hinokitiol is known for its excellent antibacterial, bactericidal, and antiseptic effects and also for being mild to the skin of the human body or the like. As already proposed, hinokitiol or its metal salt can be used as an aqueous solution for killing and disinfecting various bacteria (see, for example, Japanese Patent Application Laid-open Nos. 2000-342236, 2001-131061, and 2002-238524).

Being water-based agents, these bactericidal disinfecting agents may be left unremoved after application. Even when they are applied to the human body, no washing operation is necessary. Nevertheless, these agents present some other problems. For example, the aqueous solution dribbles when it is dispensed from a container and applied by a hand or when it is sprayed directly from a container. Besides, unlike the alcohol-based agent which dries fast, the water-based agent leaves the application area dripping wet. Particularly when the aqueous solution is applied to the human body, the hand and the application area need to be dried, or wiped by a towel or the like. It is therefore desired to provide an easy-to-use bactericidal disinfecting agent which does not encounter such problems.

An example of possible solutions is to make a foam agent. The foam agent does not dribble when dispensed from a container to a hand. Further, compared with the aqueous solution, the foam agent works in a smaller amount of use. As a result, the foam agent does not leave the hand or the application area dripping wet, and does not require a wipe-off, drying or other operation.

Concerning a skin cleansing agent, a foam agent is already disclosed in Japanese Patent Application Laid-open No. 2002-363062. However, this skin cleansing foam agent is not formulated with a bactericidal agent. Generally, it is a surfactant that causes formation of foam. However, this skin cleansing foam agent, which contains a sugar ester-type surfactant such as fatty acid ester of sucrose, turns into foam only insufficiently.

SUMMARY OF THE INVENTION

This invention aims to solve these problems. An object of the invention is to provide a composition suitable for a bactericidal, disinfecting, and cleansing agent wherein the composition turns into foam sufficiently to give a foam agent.

Through intensive researches to achieve this objective, the inventors have found that incorporation of a certain surfactant realizes a bactericidal, disinfecting, and cleansing foam agent which can turn into foam well, which can form fine and creamy foam which disappears quite fast during hand rubbing, and which does not leave sticky feel after use. Based on this finding, the inventors accomplished the invention.

Namely, this invention concerns a composition for a bactericidal, disinfecting, and cleansing foam agent which contains, as essential components, (a) at least one nonionic surfactant selected from the group consisting of polyalkylene glycol ethers and fatty acid esters of polyglycerin, (b) a bactericidal component, and (c) water.

BEST MODE FOR CARRYING OUT THE INVENTION

As a preferable embodiment of the invention, the nonionic surfactant may have a HLB of 10 or greater. The nonionic surfactant may be at least one member selected from the group consisting of fatty acid esters of polyglycerin, particularly from the group consisting of polyglycerin monolaurate and polyglycerin monomyristate. The content of the nonionic surfactant may be from 0.01 to 5.0% by weight.

As another preferable embodiment of the invention, the bactericidal component may be selected from the group consisting of hinokitiol, hinokitiol salts, and hinokitiol complexes, particularly from the group consisting of hinokitiol and alkali metal salts of hinokitiol.

As yet another preferable embodiment of the invention, the composition for a bactericidal, disinfecting, and cleansing foam agent may be free from a lower alcohol, and may also be free from an anionic surfactant, an amphoteric surfactant, and a cationic surfactant.

As still another preferable embodiment of the invention, the composition for a bactericidal, disinfecting, and cleansing foam agent may be used as a pump foam-type product.

The invention is now described in detail. The composition for a bactericidal, disinfecting, and cleansing foam agent of the invention contains, as essential components, (a) at least one nonionic surfactant selected from the group consisting of polyalkylene glycol ethers and fatty acid esters of polyglycerin, (b) a bactericidal component, and (c) water.

<Nonionic surfactant (a)>

This invention uses at least one nonionic surfactant selected from polyalkylene glycol ethers and fatty acid esters of polyglycerin. In this invention, formulation of the nonionic surfactant imparts following effects to the composition for a bactericidal, disinfecting, and cleansing foam agent. First, the composition can turn into foam well and can form fine and creamy foam. Second, this foam disappears quite fast during hand rubbing, so that no wash-off, wipe-off, or other operation is necessary. Third, the composition does not leave sticky feel after use.

The polyalkylene glycol ethers used in this invention include, for example, the compounds represented by Formula (I) below,

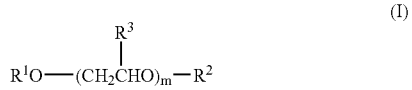

(I)

wherein each of $R^1$ and $R^2$, which may be identical or different, is a hydrogen atom, an alkyl group having 10 to 20 carbon atoms, or an alkenyl group having 10 to 20 carbon atoms, with a proviso that, if $R^1$ is a hydrogen atom, $R^2$ is not a hydrogen atom; $R^3$ is a hydrogen atom or an alkyl group having 1 to 5 carbon atoms; and m is an integer of 2 to 50.

In Formula (I) above, "the alkyl group having 10 to 20 carbon atoms", as $R^1$ and $R^2$, may be straight or branched, preferably with 12 to 18 carbon atoms. "The alkenyl group having 10 to 20 carbon atoms", as $R^1$ and $R^2$, may be straight or branched, preferably with 12 to 18 carbon atoms. "The alkyl group having 1 to 5 carbon atoms", as $R^3$, may be straight or branched, preferably with 1 to 3 carbon atoms. A preferred value of m is 10 to 30.

The polyalkylene glycol ethers in the above Formula (I) include monoethers and diethers, of which the invention prefers monoethers for their higher hydrophilicity. Further preferred among the polyalkylene glycol ethers are polyethylene glycol ethers (wherein $R^3$ is a hydrogen atom). To be specific, preferable examples of polyethylene glycol monoethers are polyoxyethylene monolauryl ether, polyoxyethylene monooleyl ether, polyoxyethylene monocetyl ether, polyoxyethylene monostearyl ether, polyoxyethylene monoisostearyl ether, polyoxyethylene monobehenyl ether, and the like. Among them, polyoxyethylene monolauryl ether, polyoxyethylene monooleyl ether, polyoxyethylene monocetyl ether, and polyoxyethylene monoisostearyl ether are preferable for their outstanding foaming property.

The fatty acid esters of polyglycerin used in the invention include, for example, the compounds represented by Formula (II) below,

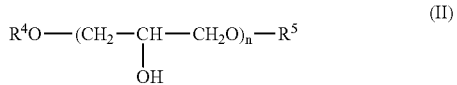

(II)

wherein each of $R^4$ and $R^5$, which may be identical or different, is a hydrogen atom, an alkylcarbonyl group having 10 to 20 carbon atoms, or an alkenylcarbonyl group having 10 to 20 carbon atoms, with a proviso that, if $R^4$ is a hydrogen atom, $R^5$ is not a hydrogen atom; and n is an integer of 2 to 20.

In Formula (II) above, "the alkylcarbonyl group having 10 to 20 carbon atoms", as $R^4$ and $R^5$, may be straight or branched, preferably with 12 to 18 carbon atoms. "The alkenylcarbonyl group having 10 to 20 carbon atoms", as $R^4$ and $R^5$, may be straight or branched, preferably with 12 to 18 carbon atoms. A preferred value of n is 4 to 12.

The fatty acid esters of polyglycerin in the above Formula (II) include monoesters and diesters, of which the invention prefers monoesters for their higher hydrophilicity. To be specific, preferable examples of fatty acid monoesters of polyglycerin are polyglycerin monolaurate, polyglycerin monomyristate, polyglycerin monopalmitate, polyglycerin monostearate, polyglycerin monoisostearate, polyglycerin monooleate, and the like. For their outstanding foaming property, polyglycerin monolaurate, polyglycerin monomyristate, and polyglycerin monooleate are preferable. On top of that, decaglycerin monolaurate and decaglycerin monomyristate are particularly preferable.

Considering the case where the composition for a bactericidal, disinfecting, and cleansing foam agent of the invention is applied to a hand, preferable nonionic surfactants are fatty acid esters of polyglycerin which are food additives. Above all, polyglycerin monolaurate and polyglycerin monomyristate are particularly preferred because they have outstanding foaming and defoaming property and can impart moist feel after use. On top of that, decaglycerin monolaurate and decaglycerin monomyristate are most preferable.

Preferably, the nonionic surfactant shows a HLB of 10 or greater, particularly from 10 to 25. If the HLB is less than 10, the nonionic surfactant shows poor solubility in water, and a resulting composition may sacrifice its ability to turn into foam.

The nonionic surfactant may be used singly or in combination.

In this invention, the composition for a bactericidal, disinfecting, and cleansing foam agent contains 0.01 to 5.0% by weight, particularly 0.1 to 1.0% by weight, of the nonionic surfactant. If its content is less than 0.01% by weight, the composition cannot turn into foam. On the other hand, if the content exceeds 5.0% by weight, the foam may become so thick as to deteriorate the defoaming property.

For the composition for a bactericidal, disinfecting, and cleansing foam agent of the invention, it is possible to employ other nonionic surfactants (e.g. lecithin, lecithin derivatives, acrylic polymer emulsifiers) in combination, to the extent that they do not inhibit the effects of the invention.

<Bactericidal Component (b)>

The bactericidal component to be used in the invention is not particularly limited as far as being soluble in water. For example, hinokitiol, hinokitiol salts, hinokitiol complexes can be mentioned as such. Examples of these salts and complexes include salts and complexes of hinokitiol with sodium, potassium, and other alkali metals; calcium, magnesium, balium, and other alkaline earth metals; aluminium, zinc, copper, iron, tin, cobalt, titanium, vanadium, and other metals; diethanolamine, triethanolamine, and other organic amines; morpholine, piperadine, and other heterocyclic amines; arginine, lysine, hystidine, and other basic amino acids, etc.

The complexes may be complex compounds of hinokitiol with aluminium compounds. The aluminium compounds may be, for example, inorganic aluminium compounds including: aluminium oxide, aluminium hydroxide, aluminic acid, chlorohydroxy aluminium, aluminium chloride, aluminium fluoride, aluminium sulfate, aluminium nitrate, aluminium borate, aluminium phosphate, potassium alum, ammonium alum, and sodium alum. In addition, the aluminium compounds may be organic aluminium compounds including aluminium salts of monobasic or dibasic carboxylic acids such as aluminium acetate, aluminium propionate, aluminium tartrate, aluminium lactate, aluminium citrate, aluminium gluconate, aluminium salicylate, and aluminium benzoate; aluminium salts of fatty acids such as aluminium laurate, aluminium myristate, aluminium palmitate, aluminium stearate, aluminium isostearate, and aluminium oleate; aluminium salts of amino acids such as aluminium glutamate, aluminium aspartate, aluminium cysteinate, aluminium sarcosinate, and aluminium β-alaninate; other organic aluminium compounds such as aluminium acyl-glutamate, aluminium salt of acylmethyltaurine, aluminium salt of acyl-β-methylalanine, aluminium polyoxyethylene alkyl ether carboxylate, aluminium sulfosuccinate, aluminium polyoxyethylene sulfosuccinate, aluminium phosphate, aluminium alkylsulfate, aluminium-substituted products of organic polymer compounds such as alginic acid, chondroitin sulfate, humic acid, hyaluronic acid, glycyrrhizic acid, polyacrylic acid, dextran sulfate, etc.

As disclosed in WO97/002025, the complex compound of hinokitiol with an aluminium compound is any of an aluminium salt of hinokitiol, a complex compound of hinokitiol with an aluminium compound, or a combination of the both, depending on the type and pH of the aluminium compound used. The complex compound can be made in the manner disclosed in WO97/002025. By way of example, hinokitiol or its salt is mixed with ethyl alcohol, water or the like at an ambient temperature. This mixed solution is poured into an aqueous solution or a non-aqueous solution such as liquid paraffin, each containing an aluminium compound, or into a mixture of the both, and mixed to obtain the complex compound.

Other bactericidal components include, for example, isopropylmethylphenol, chloroxylenol, trichlorocarbanilide, trichlorohydroxydiphenyl ether, benzalkonium chloride, cetyltrimethylammonium chloride, cetylpiperidinium chloride, benzethonium chloride, alkyl isoquinolinium bromide, chlorhexidine gluconate, KANKOSO 201, and the like.

In this invention, preferable bactericidal components are hinokitiol, hinokitiol salts, and hinokitiol complexes, of which hinokitiol and alkali salts of hinokitiol (above all, sodium salt and potassium salt of hinokitiol) are particularly preferred.

The bactericidal component may be used singly or in combination. The bactericidal component is suitably selected according to bacteria to be killed.

In this invention, the composition for a bactericidal, disinfecting, and cleansing foam agent contains 0.0001 to 1.0% by weight, particularly 0.01 to 0.5% by weight, of the bactericidal component. This content may vary with the type of bactericidal component to be used. If its content is less than 0.0001% by weight, the bactericidal effect cannot be expected. On the other hand, if the content exceeds 1.0% by weight, the composition may be harmful to the skin.

<Water (c)>

Distilled water is preferable as the water to be used in the invention. In the composition for a bactericidal, disinfecting, and cleansing foam agent of the invention, the water content is suitably adjusted to keep the contents of the nonionic surfactant and the bactericidal component within the above-defined ranges.

Regarding the composition for a bactericidal, disinfecting, and cleansing foam agent of the invention, additional components may be blended to the extent that they do not inhibit the effects of the invention. As such, it is possible to blend moisturizers such as glycerin, diglycerin, diglycerin derivatives (e.g. polyoxypropylene (9) diglyceryl ether, polyoxypropylene (14) diglyceryl ether), ethylene glycol, propylene glycol, dipropylene glycol, polyethylene glycol, polypropylene glycol, 1,3-butylene glycol, hexylene glycol, 1,2-pentanediol, 1,2-hexanediol, 1,2-octanediol, 1,2-nonanediol, 1,2-decanediol, sorbitol, xylitol, erythritol, sugar, maltitol, trehalose, and glucosyltrehalose; effective ingredients such as hyaluronic acid, sodium hyaluronate, chitin, chitosan, aloe extract, and coptis rhizome extract; and deodorant extracts such as scutellaria root extract, yeast extract, eucalyptus extract, sophora root extract, rosemary extract, clove extract, aspalathus linearis extract, sasa veitchii extract, nettle extract, green tea extract, black tea extract, oolong tea extract, amacha (hydrangea tea) extract, and persimmon extract, and the like.

The composition for a bactericidal, disinfecting, and cleansing foam agent of the invention is free from lower alcohols ($C_{1-4}$ alcohols) such as ethanol, isopropanol, propanol, and butanol. As a consequence, the composition does not irritate the skin. Further, formation of foam is not inhibited by alcohols.

The composition for a bactericidal, disinfecting, and cleansing foam agent of the invention is also free from anionic surfactants, amphoteric surfactants, and cationic surfactants. In this case, foam disappears during hand rubbing, and the composition does not irritate the skin. As a consequence, there is no need for a wash-off, wipe-off or other operation.

The composition for a bactericidal, disinfecting, and cleansing foam agent of the invention is prepared by mixing the above-mentioned components: the nonionic surfactant, the bactericidal component, the water, and, where necessary, the additional component.

The composition for a bactericidal, disinfecting, and cleansing foam agent of the invention exhibits bactericidal, disinfecting, and cleansing effects against diverse strains of bacteria, although the effects may vary with the type of bactericidal component to be used. For example, hinokitiol, hinokitiol salts, and hinokitiol complexes are effective against *P. aeruginosa*, methicillin-resistant *Staphylococcus aureus* (MRSA), *Staphylococcus aureus* (MSSA), *E. coli*, pathogenic *E. coli* 0157, *Salmonella*, vancomycin-resistant enterococci (VRE), *C. botulinum, Campylobacter*, and other anaerobic bacteria. Chlorhexidine gluconate and benzethonium chloride are effective against MSSA, *P. acnes*, etc.

When dispensed from a container to a hand, the composition for a bactericidal, disinfecting, and cleansing foam agent of the invention turns into foam and does not dribble out of the hand. Further, compared with the conventional aqueous solution-type agent, the foam-type agent works in a smaller amount of use. Hence, this foam does not leave the hand or the application area dripping wet, and no wipe-off, drying, or other operation is required. In use, the foam is spread over an application area by hand rubbing until the foam disappears. As a result, the foam can make contact with the application area evenly, and in a greater area than the aqueous solution-type agent. Furthermore, because the composition in a foamed state has a stronger bactericidal effect than the one in an aqueous solution state, the foam-type agent ensures a bactericidal effect even when used in a small amount.

The composition for a bactericidal, disinfecting, and cleansing foam agent of the invention can be supplied not only as an aerosol-type product which produces foam with the aid of a propellant, but also as a pump foam-type product which does not rely on a propellant. As it is known, the pump foam-type product produces foam by the foaming property of the surfactant itself. In this regard, the nonionic surfactant to be used in this invention has such an excellent foaming property as to realize the pump foam-type product. The pump foam-type product, which does not rely on a propellant, does not give environmental and safety threats related to the aerosol-type product.

EXAMPLES

The invention is now described in more detail in the following examples. However, the invention should not be limited to these examples.

Examples 1-3 and Comparative Examples 1-8

As Examples 1-3 and Comparative Examples 1-8, compositions for a bactericidal, disinfecting, and cleansing foam agent were prepared according to the following formulation.

|  | % by weight |
|---|---|
| Nonionic surfactant (as specified in Table 1) | 0.5 |
| Aqueous solution containing sodium salt of hinokitiol | 12.5 |
| Distilled water | 87.0 |
| Total | 100 |

(hinokitiol concentration: 250 ppm)

TABLE 1

|  | Nonionic Surfactant | HLB | Foam formation | Defoaming property | Feel after use | Total judgement |
|---|---|---|---|---|---|---|
| Example 1 | Polyglycerin-10 monolaurate | 15.5 | A | A | A | A |
| Example 2 | Polyoxyethylene lauryl ether (EO: 12) | 13.0 | A | B | A | B |
| Example 3 | Polyoxyethylene oleyl ether (EO: 20) | 17.0 | B | B | A | B |
| Comp. Ex. 1 | Sucrose stearate | 15.0 | D | — | — | D |
| Comp. Ex. 2 | PEG-5 glycerin stearate | 8.0 | D | — | — | D |
| Comp. Ex. 3 | Polyoxyethylene (12) polyoxypropylene (2) decyl ether | 12.0 | B | C | C | D |
| Comp. Ex. 4 | PEG-10 isostearate | 11.0 | D | — | — | D |
| Comp. Ex. 5 | Self-emulsifying glycerin monostearate | 8.0 | D | — | — | D |
| Comp. Ex. 6 | Polyoxyethylene (20) sorbitan monostearate | 15.0 | C | D | C | D |
| Comp. Ex. 7 | Polyoxyethylene (30) sorbitol tetraoleate | 11.5 | D | — | — | D |
| Comp. Ex. 8 | PEG-60 hydrogenated castor oil | 14.0 | D | — | — | D |

— No data

The compositions of Examples 1-3 and Comparative Examples 1-8 were filled in pump foamers (manufactured by DAIWA CAN COMPANY) to prepare bactericidal, disinfecting, cleansing foam agents. These bactericidal, disinfecting, cleansing foam agents were evaluated by the following tests. The results are shown in Table 1.

<Evaluation Methods>

1. Foam Formation

Foam was dispensed to a hand with one stroke (output: 0.4 g) of the pump foamer. By visual observation, the foam was ranked into following four grades.

A: Foam was creamy and formed abundantly.
B: Foam was relatively creamy and formed abundantly.
C: Foam was not fine and was not formed sufficiently.
D: No foam was formed.

2. Defoaming Property

Foam was dispensed to a hand with one stroke (output: 0.4 g) of the pump foamer, and rubbed in the hands. Defoaming property during the hand rubbing was ranked into following four grades.

A: Foam disappeared after hand rubbing of not longer than 15 seconds.
B: Foam disappeared after hand rubbing of 15 (exclusive) to 30 (inclusive) seconds.
C: Foam disappeared after hand rubbing of 30 (exclusive) to 60 (inclusive) seconds.
D: Foam did not disappear after hand rubbing of longer than 60 seconds.

3. Feel After Use

Foam was dispensed to a hand with one stroke (output: 0.4 g) of the pump foamer, and rubbed in the hands. Stickiness after the hand rubbing was ranked into following three grades.

A: Not sticky after use.
B: A little sticky after use.
C: Sticky after use.

As apparent from Table 1, the bactericidal, disinfecting, and cleansing foam agents prepared in Examples 1-3 excelled in all aspects of foam formation, defoaming property and feel after use.

Antibacterial Effect Test

<Test Samples>

Composition of Example 1: The composition of Example 1 was filled in a pump foamer (manufactured by DAIWA CAN COMPANY).

Control composition: A composition (nonionic surfactant: 0.5% by weight) was prepared according to Example 1, except for substituting distilled water for the aqueous solution containing sodium salt of hinokitiol. This composition was filled in a pump foamer (manufactured by DAIWA CAN COMPANY).

Ethanol gel: A hand cleansing gel made by FUMAKILLA CO. LTD. (ethanol content: 70%, formulated with aloe extract).

70% Ethanol.

<Strains>

*Escherichia coli* FMK1254

Pathogenic *Escherichia coli* 0157:H7 Sakai

*Staphylococcus aureus* ATCC25923

<Agar Medium>

MacConkey Agar (Difco) was employed for *E. coli* FMK1254 and Pathogenic *E. coli* 0157:H7 SAKAI.

Nutrient Agar (Difco) was employed for *S. aureus* ATCC25923.

<Experiment Operations>

1) The respective strains were incubated overnight in TSB at 37° C. The bacterial suspensions were diluted with physiologic saline to have a concentration of approximately $10^4$ CFU/ml each.

2) Next, 4.5 g each of the test samples were added to dishes (Composition of Example 1 and Control composition were added in a foamed state.). Thereafter, 0.5 ml each of the bacterial suspensions obtained in the process 1) was inoculated thereinto and mixed well. For every combination (12 combinations in total) of the four test samples and the three bacterial suspensions, two sample dishes were prepared in this manner.

3) Regarding the first ones of these sample dishes, the number of bacteria was counted immediately after inoculation of the bacterial suspensions, and also after one and two hours of incubation at 37° C. For incubation, the dishes were put in an incubator, with the lids slightly open. To count the number of bacteria of each strain, two agar media were respectively inoculated with 0.1 ml of the bacterial suspension and incubated for 24 hours at 37° C. Later, the number of colonies in both agar media was counted and averaged.

4) The second ones of the sample dishes prepared in the process 2) were incubated for two hours at 37° C. after inoculation of the bacterial suspensions. Thereafter, 0.5 ml each of the corresponding bacterial suspensions was again inoculated thereinto and mixed well. The number of bacteria was counted immediately after reinoculation of the bacterial suspensions, and also after one and two hours of incubation at 37° C., in the same manner as in the process 3).

The results of the antibacterial effect tests are shown in Tables 2-4.

TABLE 2

E. coli FMK1254

| Test samples | B | 0 | 1 | 2 | 0* | 1 | 2 |
|---|---|---|---|---|---|---|---|
| Composition of Example 1 | 2260 | ≦9 | ≦9 | ≦9 | 25 | ≦9 | ≦9 |
| Control composition | 2260 | 240 | 20 | 30 | 245 | 715 | 40 |
| Ethanol gel | 2260 | ≦9 | ≦9 | ≦9 | 5280 | ≦9 | ≦9 |
| 70% Ethanol | 2260 | ≦9 | ≦9 | ≦9 | 2280 | 4095 | 2195 | unit: CFU/ml
*The bacterial suspensions were inoculated again.

TABLE 3

Pathogenic E. coli O157:H7 Sakai

| Test samples | B | 0 | 1 | 2 | 0* | 1 | 2 |
|---|---|---|---|---|---|---|---|
| Composition of Example 1 | 14000 | 35 | ≦9 | ≦9 | 2700 | ≦9 | ≦9 |
| Control composition | 14000 | 4740 | 2740 | 685 | 9745 | ≧30000 | 3310 |
| Ethanol gel | 14000 | ≦9 | ≦9 | ≦9 | ≧30000 | 6440 | 125 |
| 70% Ethanol | 14000 | ≦9 | ≦9 | ≦9 | ≧30000 | ≧30000 | ≧30000 | unit: CFU/ml
*The bacterial suspensions were inoculated again.

TABLE 4

S. aureus ATCC25923

| Test samples | B | 0 | 1 | 2 | 0* | 1 | 2 |
|---|---|---|---|---|---|---|---|
| Composition of Example 1 | 2760 | 80 | ≦9 | ≦9 | 15 | ≦9 | ≦9 |
| Control composition | 2760 | 945 | 420 | 505 | 95 | 340 | 595 |
| Ethanol gel | 2760 | ≦9 | ≦9 | ≦9 | 125 | ≦9 | ≦9 |
| 70% Ethanol | 2760 | ≦9 | ≦9 | ≦9 | 180 | 75 | 45 | unit: CFU/ml
*The bacterial suspensions were inoculated again.

In Tables 2-4, "B" indicates the theoretical number of bacteria in the mixtures of the bacterial suspensions and the test samples. The symbol "*" indicates reinoculation.

As apparent from Tables 2-4, the composition of Example 1 exhibited excellent antibacterial effects against all strains of bacteria, both after two hours of inoculation and after two hours of reinoculation. In contrast, the antibacterial effects of Control composition (formulated without hinokitiol) were not sufficient against any strains of bacteria. This comparison proves that hinokitiol contributed to the remarkable antibacterial effects in Example 1.

Ethanol gel showed excellent antibacterial effects against all strains of bacteria after two hours of inoculation. Two hours after the reinoculation, its antibacterial effects were still excellent against E. coli and S. aureus, but not sufficient against pathogenic E. coli. As for 70% ethanol, the antibacterial effects were excellent against all strains of bacteria after two hours of inoculation. However, two hours after the reinoculation, its antibacterial effects were not sufficient against S. aureus and were totally lost against E. coli and pathogenic E. coli. Comparison of the antibacterial effects after two hours of reinoculation shows that 70% ethanol was inferior to the ethanol gel, the main reason of which seems to be evaporation of ethanol.

The effects of this invention are summarized below.

(1) According to this invention, the composition for a bactericidal, disinfecting, and cleansing foam agent turns into foam, thereby overcoming the problems related to the conventional aqueous solution-type agent. Namely, when dispensed from a container to a hand, the foam does not dribble out of the hand. Further, compared with the aqueous solution-type agent, the foam-type agent works in a smaller amount of use. Hence, this foam does not leave the hand or the application area dripping wet, and no wipe-off, drying, or other operation is required. In use, the foam is spread over an application area by hand rubbing until the foam disappears. As a result, the foam can make contact with the application area evenly, and in a greater area than the aqueous solution-type agent. Furthermore, because the composition in a foamed state has a stronger bactericidal effect than the one in an aqueous solution state, the foam-type agent ensures a bactericidal effect even when used in a small amount.

(2) According to this invention, the composition for a bactericidal, disinfecting, and cleansing foam agent employs at least one nonionic surfactant selected from polyalkylene glycol ethers and fatty acid esters of polyglycerin. The resulting composition can turn into foam well and can form fine and creamy foam. Further, since this foam disappears quite fast during hand rubbing, no wash-off, wipe-off or other operation is required. In particular, if the bactericidal component is hinokitiol, its metal salt or its metal complex, which are all slow-acting, it is strongly effective to omit a wash-off, wipe-off or other operation. Furthermore, the composition does not leave sticky feel after use.

A foam formulation is supplied as an aerosol-type product or a pump foam-type product. The aerosol-type product produces foam with the aid of a propellant. In contrast, the pump foam-type product is known to require a remarkable foaming property of the surfactant itself. Owing to the excellent foaming property of the above-mentioned nonionic surfactant, the composition for a bactericidal, disinfecting, and cleansing foam agent of the invention can turn into foam well, also as a pump foam-type product.

If the nonionic surfactant has a HLB of 10 or greater, the nonionic surfactant becomes more soluble in water, and a resulting composition turns into foam better.

(3) Lower alcohols are irritative to the skin and likely to cause skin roughness. In addition, an alcohol-containing composition tends to have a poorer ability to turn into foam. According to the invention, the composition for a bactericidal, disinfecting, and cleansing foam agent is free from a lower alcohol and thereby overcomes these problems.

(4) Since anionic surfactants and amphoteric surfactants have an excessive foaming property, the foam does not disappear easily during hand rubbing. Hence, use of such surfactants necessitates a wash-off, wipe-off or other operation. In addition, use of anionic surfactants and cationic surfactants, which are irritative to the skin, also necessitates a wash-off, wipe-off, or other operation. According to the invention, the composition for a bactericidal, disinfecting, and cleansing foam agent is free from anionic, amphoteric and cationic surfactants and thereby overcomes these problems.

(5) An aerosol-type product uses a propellant such as freon gas, liquefied petroleum gas, nitrogen gas, and carbon dioxide gas, thereby giving environmental and safety threats. The invention overcomes this problem by supplying the composition for a bactericidal, disinfecting, and cleansing foam agent as a pump foam-type (i.e. non-aerosol-type) product which does not rely on a propellant.

INDUSTRIAL APPLICABILITY

When in a foamed state, the composition for a bactericidal, disinfecting, and cleansing foam agent of the invention is applied simply by hand rubbing, and no wash-off, wipe-off or other operation is required. Hence, this composition can be used at any place. In particular, this composition shows an outstanding utility value where water is not available or is contaminated. Besides, it is also convenient for portable use. In comparison with the aqueous solution-type agent, the foam-type agent can make contact with the application area evenly and in a greater area. Therefore, the bactericidal effect is expected even with a small amount of foam. In conclusion, the composition for a bactericidal, disinfecting, and cleansing foam agent of the invention is highly useful from industrial point of view.

What is claimed is:

1. A bactericidal, and cleansing foam agent that does not require a water rinse for use, comprising as essential elements:
   (a) at least one non-ionic surfactant at a final concentration of 0.1% to 1%, selected from the group consisting of polyglycerin monolaurate, polyglycerin monomyristate and polyglycerin monooleate; and
   (b) a bactericidal component selected from the group consisting of hinokitiol, hinokitiol salt and hinokitiol complex;

wherein the agent further is free from a charged surfactant and is free from a lower alcohol.

2. The agent of claim 1, wherein the polyglycerin monolaurate is a decaglycerin monolaurate.

3. The agent of claim 1, wherein the polyglycerin monomyristate is a decaglycerin monomyristate.

4. The agent of claim 1, wherein the bactericidal component is a complex compound of hinokitiol with aluminum compound.

5. The agent of claim 1, wherein the bactericidal component is a sodium salt of hinokitiol.

6. The agent of claim 1, in an amount of 0.4 grams.

* * * * *